(12) United States Patent
Bouphavichith et al.

(10) Patent No.: US 6,814,716 B2
(45) Date of Patent: Nov. 9, 2004

(54) DEVICE FOR EXTERNALLY RETAINING A GASTROSTOMY FEEDING TUBE AGAINST A PATIENT AND METHOD OF USING SAID DEVICE

(75) Inventors: Laddvanh Bouphavichith, Clinton, MA (US); Michael S. H. Chu, Brookline, MA (US); Laurence D. Brenner, Northborough, MA (US); William L. Churchill, Worcester, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 215 days.

(21) Appl. No.: 10/036,187

(22) Filed: Dec. 26, 2001

(65) Prior Publication Data

US 2003/0120216 A1 Jun. 26, 2003

(51) Int. Cl.[7] .............................. A61M 5/32; A44B 1/04; A41F 1/00; A41F 1/08
(52) U.S. Cl. .......................... 604/174; 128/912; 24/546; 24/563; 24/570
(58) Field of Search ........................... 604/93.01, 94.01, 604/104, 174, 264, 523, 910; 128/200.26, 912, DIG. 26; 24/1, 3.11, 3.12, 115 R, 129 R, 130, 115 A, 115 H, 115, 545, 546, 563, 570

(56) References Cited

U.S. PATENT DOCUMENTS

| | | | |
|---|---|---|---|
| 1,409,177 A | * 3/1922 | Holman .................... 254/389 |
| 1,998,225 A | * 4/1935 | Dow .......................... 604/174 |
| 4,774,944 A | 10/1988 | Mischinski | |
| 4,834,712 A | 5/1989 | Quinn et al. | |
| 5,048,512 A | * 9/1991 | Turner et al. ............... 128/876 |
| 5,112,310 A | 5/1992 | Grobe | |
| 5,158,569 A | 10/1992 | Strickland et al. | |
| 5,167,627 A | 12/1992 | Clegg et al. | |
| 5,271,745 A | * 12/1993 | Fentress et al. ............. 604/179 |
| 5,304,145 A | * 4/1994 | Blair .......................... 604/179 |
| 5,358,488 A | 10/1994 | Surlyapa | |

* cited by examiner

Primary Examiner—Brian L. Casler
Assistant Examiner—Mark K. Han
(74) Attorney, Agent, or Firm—Kriegsman & Kriegsman

(57) ABSTRACT

A device for externally retaining a gastrostomy feeding tube comprises a clip. In one embodiment, the clip is a generally rectangular, unitary structure shaped to include a first end wall, a second end wall spaced apart from and extending parallel to the first end wall, a lower wall extending perpendicularly between and interconnecting the first end wall and the second end wall, and an upper wall having a first end connected to the first end wall and a second end spaced apart from the second end wall. The first end wall, the second end wall, the lower wall and the upper wall together define a tubing storage cavity, with the space between the upper wall and the second end wall defining an inlet to the tubing storage cavity. The first end wall has a top surface, a bottom surface and a bore extending between said top surface and said bottom surface.

17 Claims, 7 Drawing Sheets

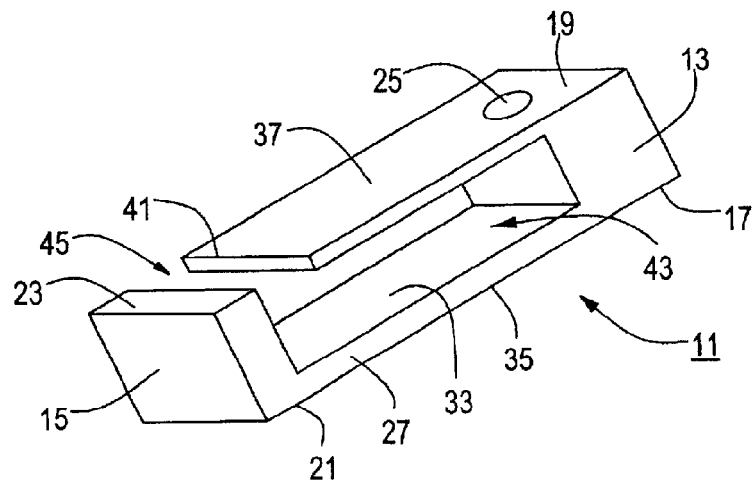
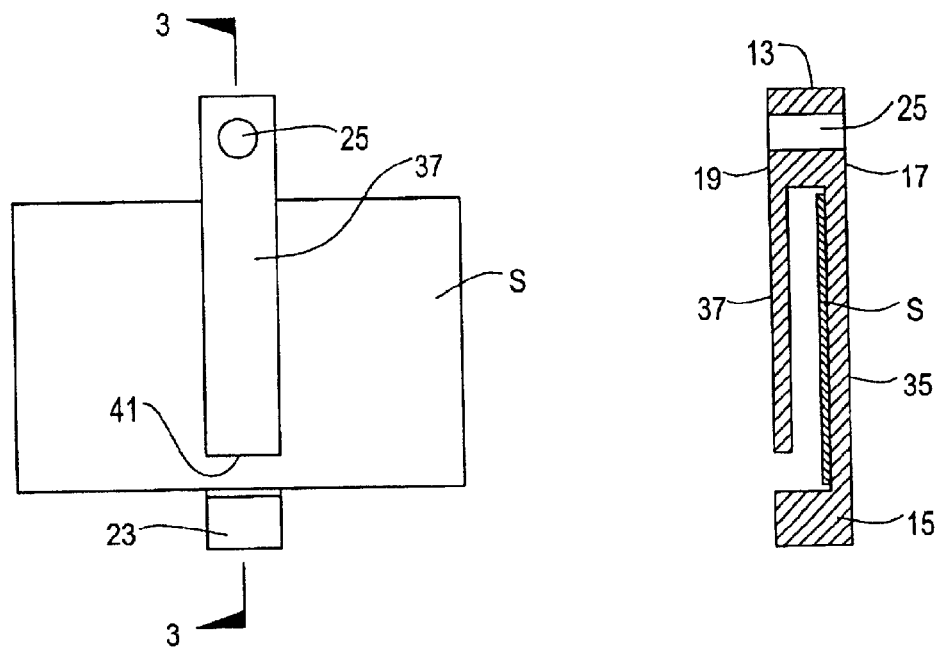
FIG. 1
FIG. 2
FIG. 3

FIG. 11(a)
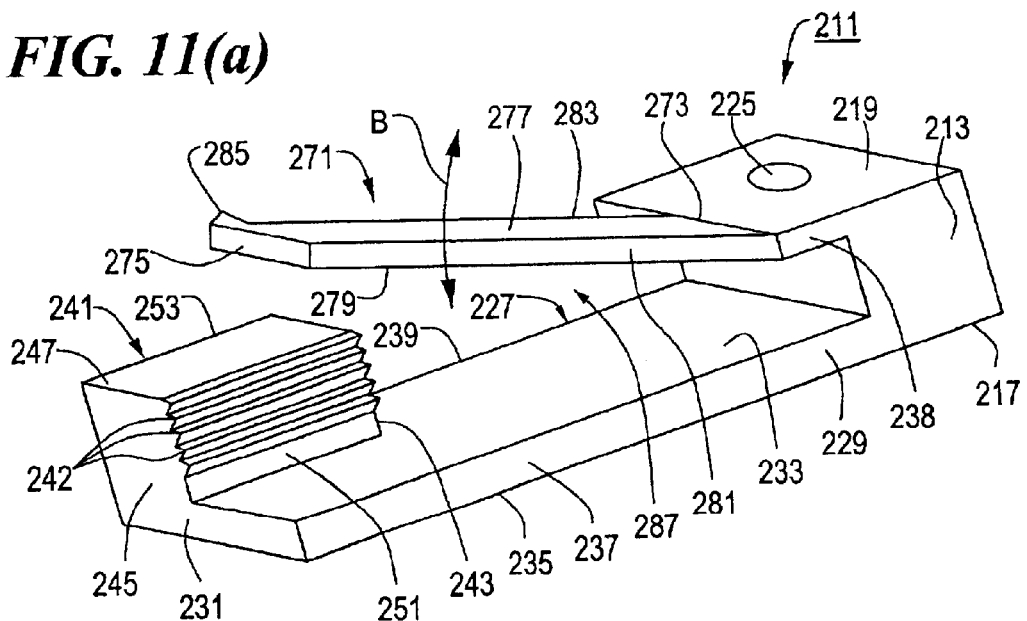
FIG. 11(b)
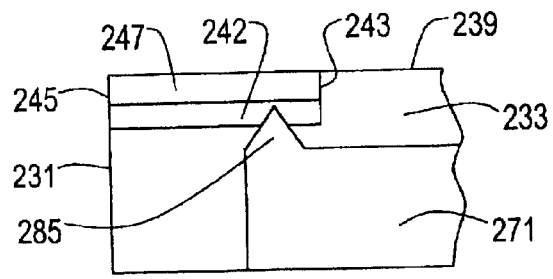
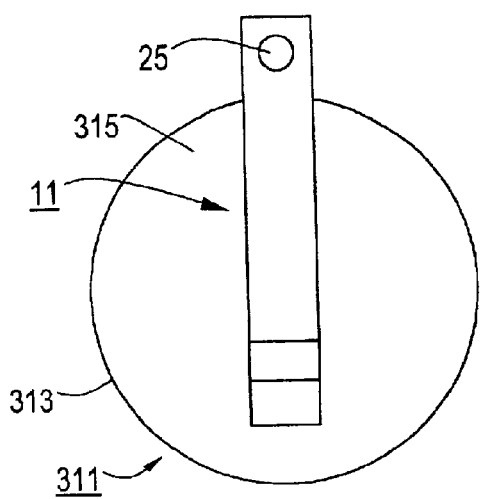
*FIG. 12*  *FIG. 14*

U S 6,814,716 B2

DEVICE FOR EXTERNALLY RETAINING A GASTROSTOMY FEEDING TUBE AGAINST A PATIENT AND METHOD OF USING SAID DEVICE

BACKGROUND OF THE INVENTION

The present invention relates generally to medical tubes of the type having a distal end implanted in a patient and a proximal end extending externally from the patient and relates more particularly to gastrostomy feeding tubes.

Certain patients are unable to take food transorally due to an inability to swallow. Such an inability to swallow may be due to a variety of reasons, such as esophageal cancer, neurological impairment and the like. Although the intravenous administration of food to such patients may be a viable short-term approach, it is not well-suited for the long-term. Accordingly, the most common approach to the long-term feeding of such patients involves gastrostomy, i.e., the creation of a feeding tract or stoma between the stomach and the upper abdominal wall. Feeding is then typically performed by administering food through a feeding tube that has been inserted into the feeding tract, with the distal end of the feeding tube extending into the stomach and being retained therein by an internal anchor or bolster and the proximal end of the feeding tube extending through the abdominal wall.

Although gastrostomies were first performed surgically, most gastrostomies are now performed using percutaneous endoscopy. In one type of percutaneous endoscopic gastrostomy (PEG) technique, the distal end of an endoscope is inserted into a patient's mouth and is passed through the esophagus into the stomach. After distension of the stomach by inflation, an incision site on the abdomen is identified and an incision is made. A needle, with an outer cannula, is inserted through the incision across the abdominal and gastric walls and into a snare loop extended from the distal end of the endoscope. While keeping the cannula in place, the needle is then removed and a flexible wire is passed through the cannula into the stomach. The endoscopic snare loop is then used to grasp the wire, the cannula is released, and the endoscope and wire are withdrawn through the esophagus and mouth of the patient. A silicone gastrostomy feeding tube, the distal end of which is attached to a silicone, dome-shaped internal bolster, is then secured to the wire and is pulled retrograde through the esophagus and into the stomach until the internal bolster engages the stomach wall and the feeding tube extends through the stomach and abdominal walls, with the proximal end of the feeding tube extending approximately one foot beyond the abdominal wall. (Over a period of several days following implantation of the feeding tube, a stable stoma tract forms around the feeding tube between the gastric and abdominal walls.)

With the internal bolster in place against the gastric wall, an external bolster is typically secured to the feeding tube to engage the abdomen so as to prevent longitudinal movement of the feeding tube within the stoma tract. Additionally, a "Y-port" adapter is typically attached to the proximal end of the feeding tube, the Y-port adapter being adapted to receive a pair of connector tips through which food and/or medications may be dispensed.

With the distal end of a gastrostomy feeding tube implanted into a patient, the proximal portion of the feeding tube extends out from the body of the patient. Typically, a considerable length of the feeding tube extends out from the body of the patient to facilitate the process of dispensing food and/or medications therethrough.

As can be appreciated, implanting a gastrostomy feeding tube in such a manner so that a substantial length of the feeding tube extends out from the patient introduces numerous drawbacks.

As a first drawback, implanting a gastrostomy feeding tube in such a manner so that a substantial length of the feeding tube extends out from the patient renders the feeding tube susceptible to the leakage of gastric fluids therethrough. Accordingly, a detachable locking clip is typically secured onto the feeding tube at a point between the external bolster and the Y-port adapter to prevent gastric fluids from escaping through the proximal end of the feeding tube when the feeding tube is not in use.

As a second drawback, implanting a gastrostomy feeding tube in such a manner so that a substantial length of the feeding tube extends out from the patient renders the feeding tube conspicuous in nature, inadvertently cumbersome and a hindrance for the patient to bend or otherwise move. Accordingly, it is well known in the art for a gastrostomy feeding tube to be manipulated into a compact configuration, such as through bending or winding of the tubing, when not used to dispense food and/or medications therethrough. Furthermore, while maintaining the tubing in its compact configuration, an adhesive, such as medical tape, is typically used to retain the tubing in its compact configuration and to temporarily secure the tubing against the body of the patient in a low profile.

SUMMARY OF THE INVENTION

It is an object of the present invention to provide a novel device for externally retaining a length of medical tubing, such as a gastrostomy feeding tube, in place against a patient, the length of medical tubing having a distal end implanted in the patient.

It is another object of the present invention to provide a device as described above that can additionally be used to store the proximal end of the medical tubing in a low profile when said medical tubing is not in use, i.e., between feedings, drainings, etc.

It is yet another object of the present invention to provide a device as described above that can be used to store the proximal end of the medical tubing, when said medical tubing is not in use, in such a way as to prevent the escape of bodily fluids therethrough.

It is still another object of the present invention to provide a device as described above that, when externally secured to a length of medical tubing implanted in a patient, minimally interferes with patient movement and causes minimal patient discomfort.

It is yet still another object of the present invention to provide a device as described above that permits the proximal end of the medical tubing to be easily removed from storage for feedings, for drainage and the like.

It is another object of the present invention to provide a device as described above that has a limited number of parts, that is inexpensive to manufacture and that is easy to use.

Accordingly, in furtherance of the above objects, as well as other objects to be described or to become apparent from the description that follows, there is provided herein a device for externally retaining a medical tube against a patient, said medical tube having a distal portion and a proximal portion, said distal portion being disposed within the patient and terminating in a distal end, said proximal portion extending externally from the patient and terminating in a proximal end, said device comprising a clip, said clip being constructed to define a bore and a tubing storage cavity, said bore being dimensioned to receive a length of the proximal portion of the medical tube therethrough, with the remainder of the proximal portion being held in a looped back configuration by said tubing storage cavity.

Said clip is preferably a generally rectangular unitary structure made of molded medical grade plastic and comprising (a) a first end wall, said first end wall having a top surface and a bottom surface, said bore extending from said top surface to said bottom surface; (b) a second end wall spaced apart from said first end wall; (c) a lower wall interconnecting said first end wall and said second end wall; and (d) an upper wall connected at a first end to said first end wall; (e) wherein said first end wall, said second end wall, said lower wall and said upper wall together define said tubing storage cavity.

In one embodiment, said upper wall further has a second end opposite to said first end, said second end being spaced apart from said second end wall so as to define a tubing inlet therebetween through which the medical tubing may be inserted into said tubing storage cavity.

In another embodiment, the device further comprises an inlet cover slidably mounted around said clip for selectively covering said tubing inlet and said clip further comprises an oversized cover stop disposed on the outer end of said second end wall for delimiting movement of said inlet cover.

In yet another embodiment, the device further comprises a disc-shaped base adapted to be mounted on a patient, said clip being mounted on said base.

In still yet another embodiment, the upper wall of the clip is pivotally connected to said first end wall, and said upper wall and said second end wall are adapted to releasably engage one another.

In still a further embodiment, the second end wall of said clip includes a top surface, said top surface being shaped to define an elongated groove adapted to receive the proximal end of the medical tube.

The present invention is also directed to a method of using the above device to externally retain a medical tube against the body of a patient. In one aspect, said method comprises the steps of: (a) providing a retaining device, said retaining device comprising a clip, said clip comprising: (i) a first end wall, said first end wall having a top surface, a bottom surface and a bore, said bore extending from said top surface to said bottom surface, (ii) a second end wall spaced apart from said first end wall, (iii) a lower wall interconnecting said first end wall and said second end wall, and (iv) an upper wall connected at a first end to said first end wall, (v) wherein said first end wall, said second end wall, said lower wall and said upper wall together define a tubing storage cavity; (b) advancing the proximal portion of the medical tube through said bore in said clip; (c) then, wrapping the proximal portion of the medical tube emergent from said bore around a side of said upper wall to form a pinch point; and (c) then, inserting the remainder of the proximal portion of the medical tube through said tubing storage cavity in a looped back configuration, said tubing storage cavity being dimensioned to retain said remainder in said looped back configuration.

Preferably, said method further comprises, after step (b), the step of securing said clip to the patient. In addition, said inserting step preferably comprises positioning the proximal end of the medical tube so that it is positioned on the same side of said upper wall as said pinch point.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts:

FIG. 1 is a perspective view of a first embodiment of a device for externally retaining a gastrostomy feeding tube against the body of a patient;

FIG. 2 is a top view of the device shown in FIG. 1, the device being shown with an adhesive strip mounted thereon;

FIG. 3 is a section view of the device and adhesive strip shown in FIG. 2 taken along lines 3—3;

FIG. 11(a) is a perspective view of a third embodiment of a device for externally retaining a gastrostomy feeding tube against the body of a patient;

FIG. 11(b) is a fragmentary top view of the device shown in FIG. 11(a);

FIG. 12 is a right side view of the device shown in FIG. 11(a), the device being shown with an adhesive strip mounted thereon;

FIG. 14 is a top view of the device shown in FIG. 13;

DETAILED DESCRIPTION OF PREFERRED EMBODIMENTS

Figure 5:
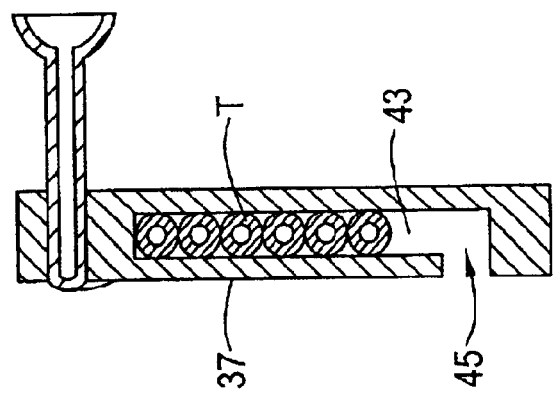
FIG. 5 is a section view of the device and gastrostomy feeding tube shown in FIG. 4 taken along lines 5—5, the distal end of the gastrostomy feeding tube being secured to an internal bolster.

Referring now to FIG. 1, there is shown a perspective view of a first embodiment of a device adapted for externally retaining a gastrostomy feeding tube in place against the body of a patient, the device being constructed according to the teachings of the present invention and being identified generally by reference numeral 11. (Although device 11 is described herein as being adapted for use with a gastrostomy feeding tube, it is to be understood that device 11 is not limited to use with gastrostomy feeding tubes and may be used with many other types of medical tubes used for feeding, drainage or the like.)

Device 11, which is a low-profile, unitary clip preferably constructed from a medical grade plastic using conventional manufacturing techniques, is shaped to include a first end wall 13 and a second end wall 15, end walls 13 and 15 being disposed in a parallel, spaced apart orientation. First end wall 13, which is generally rectangular, includes a bottom surface 17 and a top surface 19. Second end wall 15, which is also generally rectangular, includes a bottom surface 21 and a top surface 23. A generally cylindrical bore 25 is provided in first end wall 13 and extends longitudinally from bottom surface 17 to top surface 19. As will be seen below, bore 25 is adapted to receive a gastrostomy feeding tube therethrough.

Device 11 is additionally shaped to include an elongated generally rectangular lower wall 27, wall 27 extending perpendicularly between and interconnecting first end wall 13 and second end wall 15. Lower wall 27 has a top surface 33 and a bottom surface 35, bottom surface 35 of lower wall 27 forming a continuous surface with bottom surface 17 of first end wall 13 and bottom surface 21 of second end wall 15.

Device 11 is further shaped to include an elongated generally rectangular upper wall 37. Upper wall extends perpendicularly between first end wall 13 and second end wall 15 and is connected at a first end thereof to first end wall 13. A second end 41 of upper wall 37 is spaced a short distance away from second end wall 15 for reasons to become apparent below.

First end wall 13, second end wall 15, lower wall 27 and upper wall 37 together define a generally rectangular tubing storage cavity 43, the purpose of cavity 43 to be described below. In addition, the space between second end 41 of upper wall 37 and second end wall 15 is shaped to define a tubing inlet 45, inlet 45 communicating with tubing storage cavity 43. As will be described below in further detail, inlet 45 and cavity 43 are dimensioned to permit a length of gastrostomy tubing to be fed through tubing inlet 45 and stored in tubing storage cavity 43 in a looped back configuration so as to hold the external portion of the gastrostomy feeding tube in a compact and low profile configuration against the body of a patient.

Referring now to FIGS. 2 and 3, there are shown top and section views, respectively, of device 11 and a strip S of one-sided adhesive tape, strip S having an adhesive (not shown) applied to its bottom surface for securing device 11 to a patient. As can be seen best in FIG. 3, strip S preferably extends laterally through tubing storage cavity 43, with the intermediate portion of strip S being in direct contact with top surface 33 of device 11.

Figure 4:
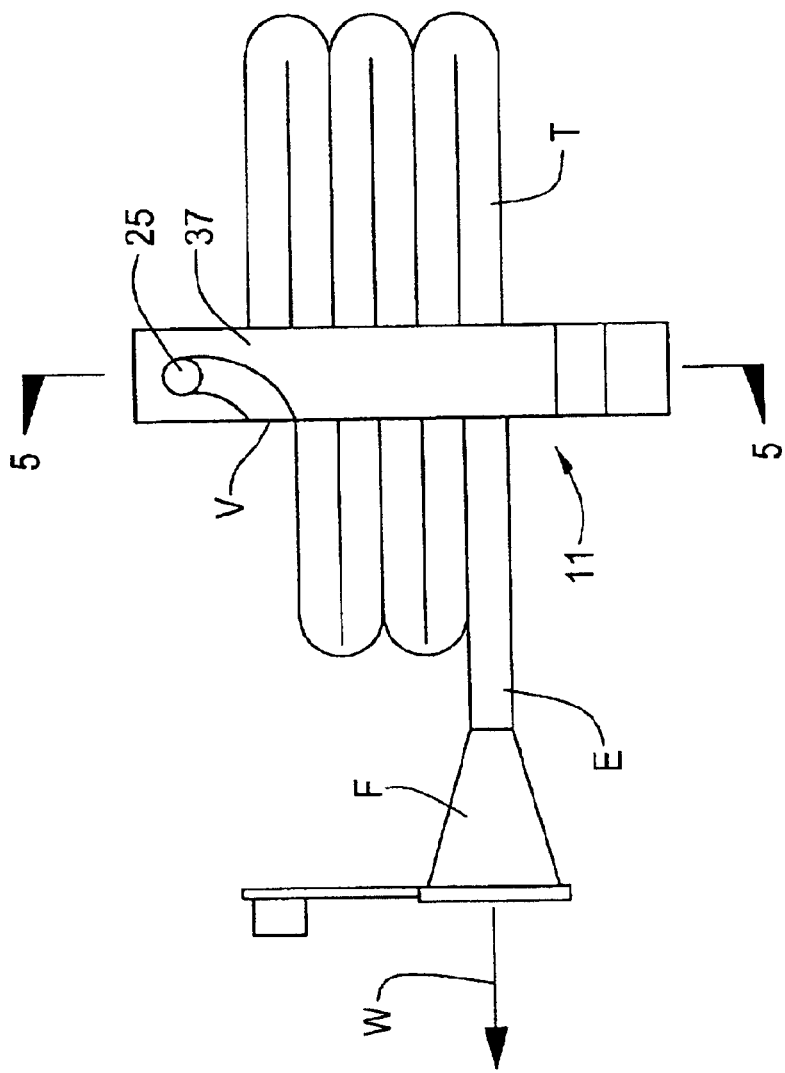
FIG. 4 is a top view of the device shown in FIG. 1, the device being shown attached to a gastrostomy feeding tube, with the proximal end of the gastrostomy feeding tube being looped back and forth within the storage cavity of the device.
Figure 6:
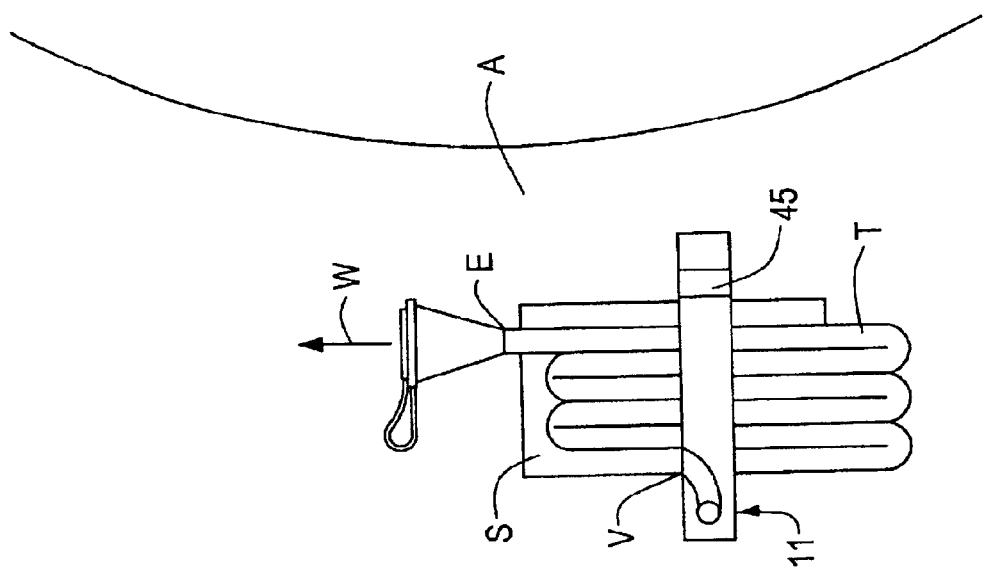
FIG. 6 is a top plan view of the device and gastrostomy feeding tube shown in FIG. 4, the device being shown mounted with a strip of adhesive tape onto the outer surface of the body of a patient into whom the distal end of the gastrostomy feeding tube has been implanted.
Figure 7:
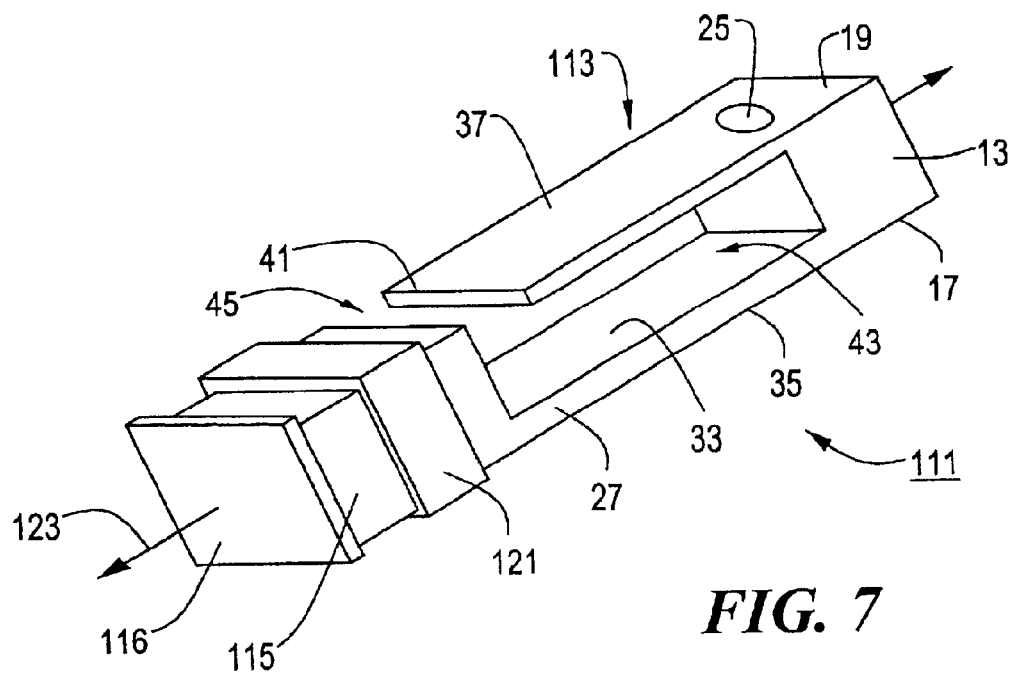
FIG. 7 is a perspective view of a second embodiment of device for externally retaining a gastrostomy feeding tube against the body of a patient.

Referring now to FIGS. 4 through 6, there are shown various views illustrating the manner in which device 11 may be used to externally retain a gastrostomy feeding tube T in place on a patient, with the externally exposed (or proximal) portion of tube T that extends beyond the abdominal wall A of the patient being stored in a compact and low profile configuration. (For ease of understanding, strip S is not shown in FIGS. 4 and 5.)

First, tube T is coupled to device 11 by inserting the proximal end E of gastrostomy feeding tube T through tubing bore 25. With tube T thus coupled to device 11, device 11 is preferably secured to the abdominal wall A of a patient with adhesive strip S. This is preferably accomplished by applying the intermediate portion of adhesive strip S to top surface 33 of lower wall 27, with the opposing lateral portions of adhesive strip S being pressed against the patient. (As seen best in FIG. 6, device 11 is preferably secured to abdominal wall A of the patient at an angle perpendicular to the spine of the patient so as to allow the patient to comfortably achieve a wide range of upper body motion without being jabbed by device 11.)

With the external portion of gastrostomy feeding tube T thus inserted through tubing hole 25 and with device 11 thus secured to the patient, gastrostomy feeding tube T is then bent and inserted laterally through tubing storage cavity 43 so as to create a pinch point valve V in feeding tube T, as seen most clearly in FIGS. 4 and 6. Specifically, pinch point valve V is created by pulling tubing T taut against a side surface of upper wall 37. As can be appreciated, the creation of pinch point valve V in tube T is beneficial in that pinch point valve V serves to preclude the leakage of gastric fluids through feeding tube T.

With pinch point valve V thus formed, the external portion of tubing T is fed through tubing inlet 45 and into tubing storage cavity 43, where said tubing is bent in a looped back configuration to form a plurality of parallel subsections of tubing T which extend laterally through tubing storage cavity 43 in a side-by-side relationship. As can be appreciated, by arranging gastrostomy feeding tube T in the aforementioned looped back configuration, feeding tube T can be stored in a compact and low-profile manner. With feeding tube T thus stored, a fitting F may be inserted into proximal end E.

It should be noted that gastrostomy feed tube T is preferably repeatedly looped back through tubing storage cavity 43 in such a manner that proximal end E and fitting F are disposed on the same side of device 11 as is pinch point valve V, as seen most clearly in FIGS. 4 and 6. In this manner, simply by pulling fitting F away from device 11, as represented by arrow W in FIG. 4, one can completely straighten feeding tube T and remove it from cavity 43. (By contrast, if proximal end E and fitting F were positioned on the opposite side of device 11 relative to pinch point V, one would first have to thread end E and fitting F through cavity 43 before being able to completely straighten tube T.) With tube T thus straightened, food and/or medications can be delivered to the patient via tube T by inserting the distal end of a food and/or medication delivery device (not shown) into fitting F. When the dispensing of food and/or medications into the patient through tube T is complete, the distal end of the delivery device is removed from fitting F, and tube T is once again stored in cavity 43 in the above-described looped back manner, with end E and fitting F preferably being positioned on the same side of device 11 as pinch point valve V.

As can readily be appreciated, one desirable feature of device 11 is that tube T can be repeatedly stored and straightened—all without removing tube T from bore 25 of device 11 and without removing device 11 from the patient. Accordingly, once tube T has been inserted through bore 25 and device 11 has been secured to the patient, typically with a strip of adhesive tape, these steps need not be repeated, regardless of the number of times tube T is alternately stored in cavity 25 or straightened. This is a distinct advantage over the conventional method of storing the proximal end of a gastrostomy feeding tube which, as noted above, typically involves manipulating the end of the tube into a compact configuration and then using a strip of adhesive tape to secure the compacted end to the patient. Moreover, as can readily be appreciated, the manipulating step and the securing step of the conventional storage method are particularly difficult for the patient to perform unassisted. Accordingly, another advantage of device 11 is that it facilitates unassisted storage and deployment of the tube by the patient (as well as simplifying use by a nurse).

Referring now to FIGS. 7 through 10, there are shown various views of a second embodiment of a device for externally retaining a gastrostomy feeding tube in place against the body of a patient, the device being constructed according to the teachings of the present invention and being identified generally by reference numeral 111. (Although device 111 is described herein as being adapted for use with a gastrostomy feeding tube, it is to be understood that device 111 is not limited to use with gastrostomy feeding tubes and may be used with many other types of medical tubes used for feeding, drainage or the like.)

Device 111 comprises a clip 113, clip 113 being identical to device 11, except that (i) clip 113 is shaped to define an end wall 115 that extends longitudinally outwardly a greater distance than does end wall 15 and (ii) clip 113 is additionally shaped to include an oversized cover stop 116 formed on the outer end of end wall 115.

Figure 8:
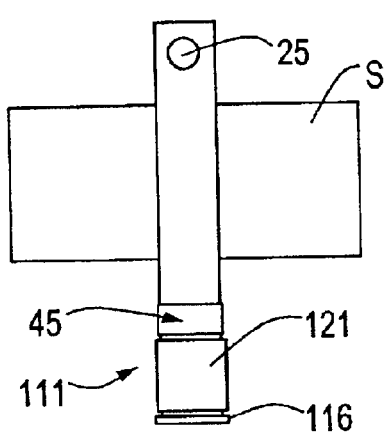
FIG. 8 is a top view of the device shown in FIG. 7, the device being shown with an adhesive strip mounted thereon and with the inlet cover disposed at a first position.
Figure 9:
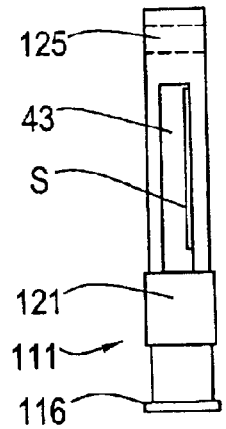
FIG. 9 is a right side view of the device shown in FIG. 7, the device being shown with an adhesive strip mounted thereon and with the inlet cover disposed at a second position.
Figure 10:
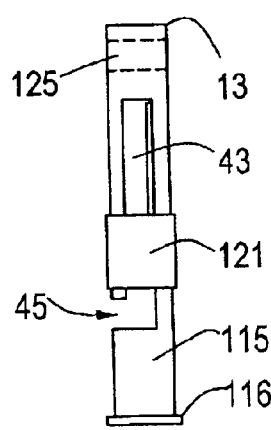
FIG. 10 is a right side view of the device shown in FIG. 7, the device being shown with an adhesive strip mounted thereon and with the inlet cover disposed at a third position.

Device 111 also comprises a rectangular inlet cover 121, inlet cover 121 being slidably mounted on clip 113 for movement along the longitudinal axis 123 of clip 113. Movement of inlet cover 121 along clip 113 in the direction away from end 13 is delimited by cover stop 116, as shown in FIG. 8. With inlet cover 121 thus disposed against cover stop 116, tubing inlet 45 is open, thereby enabling a length of gastrostomy feeding tube to be passed therethough into cavity 43. Inlet cover 121 can also be moved longitudinally away from cover stop 116 until positioned over tubing inlet 45, as shown in FIG. 9, thereby precluding a length of gastrostomy feeding tube from either entering or exiting tubing storage cavity 43 through tubing inlet 45. In addition, inlet cover 121 can be further moved longitudinally away from cover stop 116 until disposed between tubing inlet 45 and first end wall 13, as shown FIG. 10. With inlet cover 121 thus disposed between tubing inlet 45 and first end wall 13, inlet cover 121 can be wedged against a portion of a feed tube positioned within tubing storage cavity 43, thereby securing the feed tube within the tubing storage cavity 43.

Device 111 can be used in substantially the same manner as device 11 to retain the exterior portion of a gastrostomy feeding tube in a compact and low profile configuration against the abdominal wall of a patient. The principal distinction in use between device 111 and device 11 is that device 111 includes inlet cover 121, which can be moved along longitudinal axis 123 to close off tubing inlet 45 and/or to wedge against a length of feed tube disposed within tubing storage cavity 43 to retain the length of feed tube within tubing storage cavity 43.

Referring now to FIGS. 11(a), 11(b) and 12, there are shown various views of a third embodiment of a device for externally retaining a gastrostomy feeding tube against a patient, the clip being constructed according to the teachings of the present invention and being identified generally by reference numeral 211. (Although device 211 is described herein as being adapted for use with a gastrostomy feeding tube, it is to be understood that device 211 is not limited to use with gastrostomy feeding tubes and may be used with many other types of medical tubes used for feeding, drainage or the like.)

Device 211, which is a low-profile, unitary clip preferably constructed from a medical grade plastic using conventional manufacturing techniques, is shaped to include a first end wall 213, end wall 213 being generally rectangular and having a bottom surface 217 and a top surface 219. A tubing hole 225 is formed in end wall 213 and extends between bottom surface 217 and top surface 219, tubing hole 225 being dimensioned to receive a gastrostomy feeding tube therethrough.

Device 211 is also shaped to include an elongated lower wall 227. Lower wall 227, which is generally rectangular in shape, includes a first end 229, a second end 231, a top surface 233, a bottom surface 235, a front side 237 and a rear side 239. Lower wall 227 is joined to end wall 213 at end 229 in such a way that bottom surface 235 of wall 227 and bottom surface 217 of wall 213 form a continuous surface.

Device 211 is additionally shaped to include a block 241, block 241 being formed on top surface 233 of wall 227 proximate to end 231. Block 241, which is generally rectangular in shape, has a first end 243, a second end 245, a top surface 247, a bottom surface, a front side 251 and a rear side 253. Rear side 253 and end 245 of block 241 are flush with rear side 239 and end 231 of wall 227, respectively, with front side 251 of block 241 being disposed about one-eighth of the width across wall 227. A plurality of horizontally-disposed teeth 242 are formed on front side 251, the purpose of teeth 242 to become apparent below.

Lastly, device 211 is also shaped to include an elongated arm 271, arm 271 being generally rectangular in shape and including a first end 273, a second end 275, a top surface 277, a bottom surface 279, a front side 281 and a rear side 283. Arm 271 is joined to end wall 213 at first end 273 and is adapted for pivotal movement along the path defined by arrow B in FIG. 11(a). Front side 281 of arm 271 is flush with a front side 238 of wall 213, with rear side 283 of arm 271 being disposed about seven-eighths of the width across wall 213. A rearwardly-extending pawl 285 is formed on arm 271 proximate to second end 275, pawl 285 being adapted to engage teeth 242 of block 241 in a ratchet-type manner so that arm 271 can be brought from an open position, as shown in FIGS. 11(a) and 12, to one of a variety of closed positions defining a tubing storage cavity 287. Although not shown in the present embodiment, arm 271 may be rearwardly biased to ensure engagement of pawl 285 with teeth 242. To move arm 271 from a closed position to an open position, one must disengage pawl 285 from teeth 242. This may be done by applying an upward force to arm 271 and/or by applying a forward lateral force to arm 271.

Although device 211 is shown as having a ratchet-type arrangement for releasably securing arm to block 241, device 211 could alternatively be provided with other types of releasable interlocking arrangements, such as a snap-fit arrangement or the like.

Device 211 is used in a similar manner as device 11 to externally retain the exterior portion of a gastrostomy feeding tube in a compact and low profile configuration against the abdominal wall of a patient. The principal distinction in the manner in which the two devices are used is that device 211 includes a pivotally mounted arm 271 for facilitating access to tubing storage cavity 287. Specifically, arm 271 is preferably disposed in its open position as the length of feeding tube is repeatedly bent into its looped back configuration extending through cavity 287. With the length of feeding tube thus bent and positioned in cavity 287, arm 271 is then moved to a closed position, thereby precluding the length of feeding tube from exiting tubing storage cavity 287 through its top.

Figure 13:
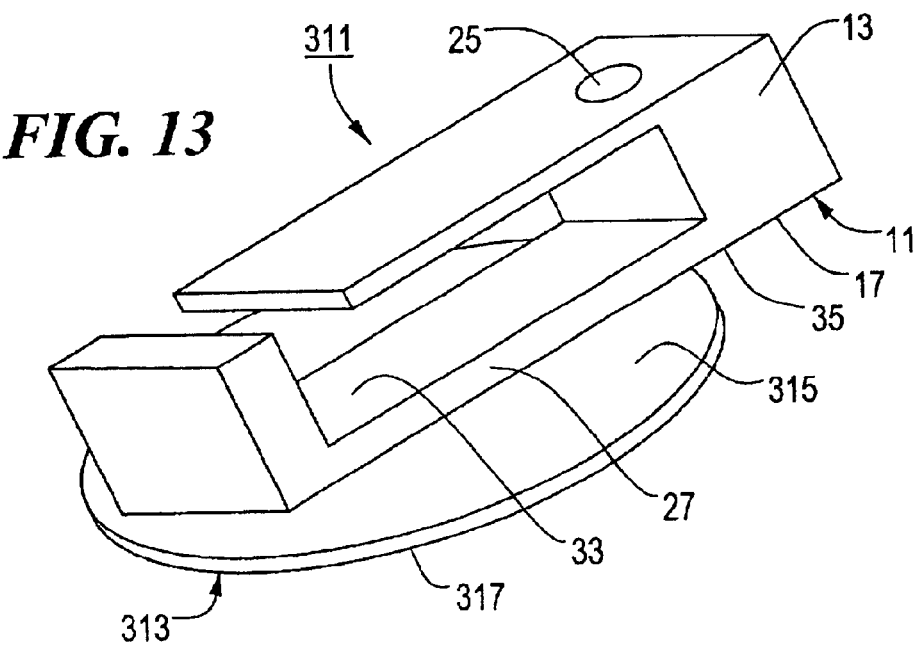
FIG. 13 is a perspective view of a fourth embodiment of a device for externally retaining a gastrostomy feeding tube against the body of a patient.

Referring now to FIGS. 13 and 14, there are shown perspective and top views, respectively, of a fourth embodiment of a device for externally retaining a gastrostomy feeding tube against the body of a patient, the device being constructed according to the teachings of the present invention and being identified generally by reference numeral 311.

Device 311 comprises clip 11 and a base 313, base 313 being secured to clip 11.

Base 313 is a flexible, disc-shaped member which includes a top adhesive surface 315 and a bottom adhesive surface 317. Top adhesive surface 315 is applied directly to the bottom of clip 11, and bottom adhesive surface 317 is adapted to be applied directly to a patient. It should be noted that base 313 does not cover tubing hole 25 at first end 17 of first end wall 13. As a result, the entry site of the gastrostomy feed tube into the body of the patient can be readily cleaned and maintained without interference of clip 11.

Although clip 11 and base 313 are separately formed and adhesively joined together in the above-described manner, it can readily be appreciated that clip 11 and base 313 could be formed as a unitary structure, for example, using conventional molding techniques. It should also be understood that the adhesive used to adhere base 313 to a patient could be separately provided.

Device 311 is used in substantially the same manner as clip 11 to retain the exterior portion of a gastrostomy feeding tube in a compact and low profile configuration against the abdominal wall of a patient. The principal distinction between device 311 and clip 11 is that device 311 is secured to the body of a patient using base 313 whereas clip 11 is secured to the body of a patient using a strip of adhesive material applied over interior surface 33 of inner wall 27.

Figure 15:
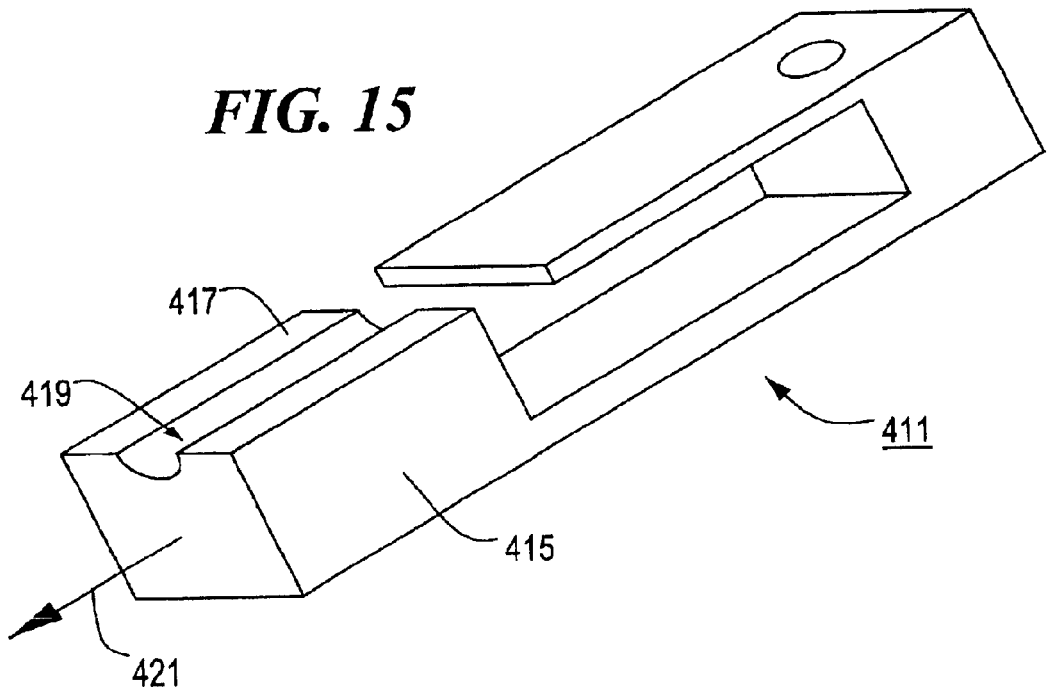
FIG. 15 is a perspective view of a fifth embodiment of a device for externally retaining a gastrostomy feeding tube against the body of a patient.
Figure 17:
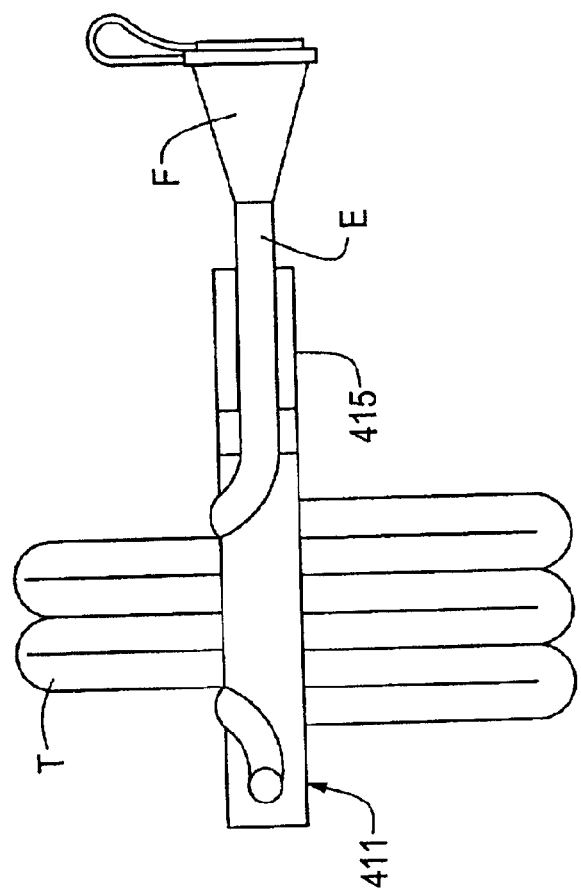
FIG. 17 is a top view of the device shown in FIG. 15, the device being shown with a gastrostomy feeding tube looped back within the storage area of the device and with the proximal end of the feeding tube retained within the groove formed in the top surface of the second end wall.
Figure 16:
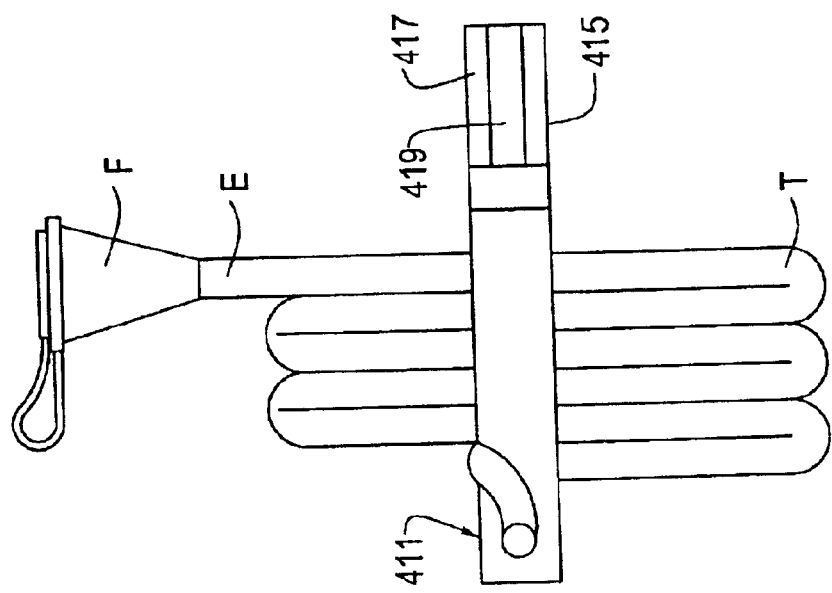
FIG. 16 is a top view of the device shown in FIG. 15, the device being shown with a gastrostomy feeding tube looped back within the storage area of the device.

Referring now to FIGS. 15 through 17, there are shown various views of a fifth embodiment of a device for externally retaining a gastrostomy feeding tube on the body of a patient, the device being constructed according to the teachings of the present invention and being identified generally by reference numeral 411.

Device 411 is similar in most respects to device 11, the principal difference between the two devices being that device 411 comprises a second end wall 415 which differs in construction from second end wall 15 of device 11.

Specifically, second end wall 415 of clip 411 comprises a top surface 417 which is shaped to define an elongated groove 419. Groove 419 is generally semi-circular in shape and extends along top surface 417 at an angle parallel to the longitudinal axis 421 of second end wall 415. Groove 419 is sized and shaped so that the proximal portion of feeding tube T can be releasably retained therewithin by a press-fit.

Device 411 functions in substantially the same manner as device 11 to retain the exterior portion of a gastrostomy feeding tube in a compact and low profile configuration against the abdominal wall of a patient. The principal distinction in the functionality between device 411 and device 11 is that device 411 additionally retains the proximal portion of the feeding tube T within groove 419. With the proximal portion of the feeding tube T thus disposed within groove 419, as shown in FIG. 17, fitting F is less likely to jab the patient when the patient bends over than may be the case with fitting F positioned as shown in FIG. 16.

The embodiments of the present invention described above are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising a clip wherein said clip comprises:
   (a) a first end wall, said first end wall having a top surface, a bottom surface and a bore, said bore extending from said top surface to said bottom surface, said bore being dimensioned to receive a length of the proximal portion of the medical tube therethrough;
   (b) a second end wall spaced apart from said first end wall;
   (c) a lower wall interconnecting said first end wall and said second end wall; and
   (d) an upper wall connected at a first end to said first end wall;
   (e) wherein said first end wall, said second end wall, said lower wall and said upper wall together define a tubing storage cavity, with the remainder of the proximal portion of the medical tube being held in a looped back configuration by said tubing storage cavity and wherein said upper wall further has a second end opposite to said first end, said second end being spaced apart from said second end wall so as to define a tubing inlet therebetween through which the medical tubing may be inserted into said tubing storage cavity.

2. The device as claimed in claim 1 wherein said clip is a unitary structure.

3. The device as claimed in claim 2 wherein said clip is generally rectangular in shape.

4. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising:
   (a) a clip, said clip comprising
      (i) a first end wall, said first end wall having a ton surface, a bottom surface and a bore, said bore extending from said ton surface to said bottom surface, said bore being dimensioned to receive a length of the proximal portion of the medical tube therethrough, (ii) a second end wall spaced apart from said first end wall, (iii) a lower wall interconnecting said first end wall and said second end wall, and (iv) an upper wall connected at a first end to said first end wall, (v) wherein said first end wall, said second end wall, said lower wall and said upper wall together define a tubing storage cavity, with the remainder of the proximal portion of the medical tube being held in a looped back configuration by said tubing storage cavity and wherein said upper wall further has a second end opposite to said first end, said second end being spaced apart from said second end wall so as to define a tubing inlet therebetween through which the medical tubing may be inserted into said tubing storage cavity; and (b) an inlet cover slidably mounted around said clip for selectively covering said tubing inlet.

5. The device as claimed in claim 4 wherein said clip further comprises an oversized cover stop disposed on the outer end of said second end wall for delimiting movement of said inlet cover.

6. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising:

(a) a clip, said clip comprising (i) a first end wall, said first end wall having a top surface, a bottom surface and a bore, said bore extending from said top surface to said bottom surface, said bore being dimensioned to receive a length of the proximal portion of the medical tube therethrough, (ii) a second end wall spaced apart from said first end wall, (iii) a lower wall interconnecting said first end wall and said second end wall, and (iv) an upper wall connected at a first end to said first end wall;

(v) wherein said first end wall, said second end wall, said lower wall and said upper wall together define a tubing storage cavity, with the remainder of the proximal portion of the medical tube being held in a looped back configuration by said tubing storage cavity; and (b) a base adapted to be mounted on a patient, said clip being mounted on said base.

7. The device as claimed in claim 6 wherein said base has an adhesive top surface and an adhesive bottom surface.

8. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising a clip wherein said clip comprises:

(a) a first end wall, said first end wall having a top surface, a bottom surface and a bore, said bore extending from said top surface to said bottom surface, said bore being dimensioned to receive a length of the proximal portion of the medical tube therethrough;

(b) a second end wall spaced apart from said first end wall;

(c) a lower wall interconnecting said first end wall and said second end wall; and (d) an upper wall connected at a first end to said first end wall, wherein said upper wall is pivotally connected to said first end wall for vertical movement and wherein said first end wall, said second end wall, said lower wall and said upper wall together define a tubing storage cavity, with the remainder of the proximal portion of the medical tube being held in a boned back configuration by said tubing storage cavity.

9. The device as claimed in claim 8 wherein said upper wall and said second end wall are adapted to releasably engage one another.

10. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising a clip wherein said clip comprises:

(a) a first end wall, said first end wall having a top surface, a bottom surface and a bore, said bore extending from said top surface to said bottom surface, said bore being dimensioned to receive a length of the proximal portion of the medical tube therethrough;

(b) a second end wall spaced apart from said first end wall, wherein said second end wall is provided with a plurality of vertically-stacked teeth;

(c) a lower wall interconnecting said first end wall and said second end wall; and (d) an upper wall connected at a first end to said first end wall, wherein said first end wall, said second end wall, said lower wall and said upper wall together define a tubing storage cavity, with the remainder of the proximal portion of the medical tube being held in a looped back configuration by said tubing storage cavity, wherein said upper wall is pivotally connected to said first end wall and wherein said upper wall is provided with a pawl adapted to releasably engage said vertically-stacked teeth.

11. A device for externally retaining a medical tube against a patient, said medical tube having a distal portion and a proximal portion, said distal portion being disposed within the patient and terminating in a distal end, said proximal portion extending externally from the patient and terminating in a proximal end, said device comprising a clip wherein said clip comprises:

(a) a first end wall, said first end wall having a ton surface, a bottom surface and a bore, said bore extending from said top surface to said bottom surface, said bore being dimensioned to receive a length of the proximal portion of the medical tube therethrough;

(b) a second end wall spaced apart from said first end wall, wherein said second end wall of said clip includes a top surface, said top surface being shaped to define an elongated groove adapted to receive the proximal end of the medical tube;

(c) a lower wall interconnecting said first end wall and said second end wall; and (d) an upper wall connected at a first end to said first end wall, wherein said first end wall, said second end wall, said lower wall and said upper wall together define a tubing storage cavity, with the remainder of the proximal portion of the medical tube being held in a looped back configuration by said tubing storage cavity.

12. The device as claimed in claim 11 wherein said groove extends generally parallel to said lower wall.

13. A method for externally retaining a medical tube against a patient, said medical tube having a distal portion and a proximal portion, said distal portion being disposed within the patient and terminating in a distal end, said proximal portion extending externally from the patient and terminating in a proximal end, said method comprising the steps of:

(a) providing a retaining device comprising a clip, said clip comprising a pair of end walls, an upper wall, a lower wall and a pair of open sides, wherein said pair of end walls, said upper wall and said lower wall together define a tubing storage cavity and wherein one of said end walls is shaped to include a bore, said bore being dimensioned to receive a length of the proximal portion of the medical tube therethrough, with the remainder of the proximal portion being retained by said tubing storage cavity;

(b) advancing the proximal portion of the medical tube through said bore in said clip; and (c) retaining the remainder of the proximal portion of the medical tube using said tubing storage cavity.

14. A method for externally retaining a medical tube against a patient, said medical tube having a distal portion and a proximal portion, said distal portion being disposed within the patient and terminating in a distal end, said proximal portion extending externally from the patient and terminating in a proximal end, said method comprising the steps of:

(a) providing a retaining device, said retaining device comprising a clip, said clip comprising:

(i) a first end wall, said first end wall having a top surface, a bottom surface and a bore, said bore extending from said top surface to said bottom surface, (ii) a second end wall spaced apart from said first end wall, (iii) a lower wall interconnecting said first end wall and said second end wall, and (iv) an upper wall connected at a first end to said first end wall, (v) wherein said first end wall, said second end wall, said lower wall and said upper wall together define a tubing storage cavity;

(b) advancing the proximal portion of the medical tube through said bore in said clip;

(c) then, wrapping the proximal portion of the medical tube emergent from said bore around a side of said upper wall to form a pinch point; and (c) then, inserting the remainder of the proximal portion of the medical tube through said tubing storage cavity in a looped back configuration, said tubing storage cavity being dimensioned to retain said remainder in said looped back configuration.

15. The method as claimed in claim 14 further comprising after step (b), the step of securing said clip to the patient.

16. The method as claimed in claim 14 wherein said inserting step comprises positioning the proximal end of the medical tube so that it is positioned on the same side of said upper wall as said pinch point.

17. The method as claimed in claim 14 wherein the medical tube is a gastrostomy feeding tube.

* * * * *